(12) United States Patent
Rubin et al.

(10) Patent No.: US 11,045,093 B2
(45) Date of Patent: Jun. 29, 2021

(54) SENSOR UNIT

(71) Applicant: Healbe Corporation, Redwood City, CA (US)

(72) Inventors: Mikhail S. Rubin, St. Petersburg (RU); Igor L. Misjuchenko, St. Petersburg (RU); Oleg M. Gerasimov, Leningradskaya obl. (RU); Aleksandr S. Strelnikov, St. Petersburg (RU)

(73) Assignee: Healbe Corporation, Redwood City, CA (US)

( * ) Notice: Subject to any disclaimer, the term of this patent is extended or adjusted under 35 U.S.C. 154(b) by 73 days.

(21) Appl. No.: 15/796,364

(22) Filed: Oct. 27, 2017

(65) Prior Publication Data
US 2018/0049651 A1    Feb. 22, 2018

Related U.S. Application Data

(63) Continuation of application No. PCT/RU2016/000269, filed on May 4, 2016.

(30) Foreign Application Priority Data

May 6, 2015 (RU) .......................... RU2015117066

(51) Int. Cl.
*A61B 5/0205* (2006.01)
*A61B 5/024* (2006.01)
(Continued)

(52) U.S. Cl.
CPC ........ *A61B 5/0205* (2013.01); *A61B 5/02438* (2013.01); *A61B 5/0531* (2013.01);
(Continued)

(58) Field of Classification Search
None
See application file for complete search history.

(56) References Cited

U.S. PATENT DOCUMENTS

| | | | |
|---|---|---|---|
| 6,491,647 B1 * | 12/2002 | Bridger | ................. A61B 5/021 128/900 |
| 2004/0039254 A1 | 2/2004 | Stivoric et al. | |

(Continued)

FOREIGN PATENT DOCUMENTS

| | | |
|---|---|---|
| CN | 1723842 A | 1/2006 |
| CN | 103505190 A | 1/2014 |

(Continued)

OTHER PUBLICATIONS

International Search Report from International Application No. PCT/RU2016/000269, filed May 4, 2016, dated Aug. 25, 2016.

*Primary Examiner* — Michael W Kahelin
*Assistant Examiner* — Elizabeth K So
(74) *Attorney, Agent, or Firm* — Patentbar International, P.C.

(57) ABSTRACT

A sensor unit for use in devices for simultaneous measurement of signals associated with human tissue impedance and pressure to identify human hemodynamic parameters. The sensor unit of the device attached to a skin surface segment of a human body includes a base with a recess, in which a piezoelectric element of pressure sensor is installed. The unit also has a flexible membrane mounted on the base and overlapping said recess. First and second electrodes are attached to the outer surface of the membrane. The first electrode is mounted opposite the recess and is capable of moving together with the membrane. The second immovable electrode surrounds the first electrode. A central support is mounted between the first electrode and the piezoelectric element. Connected to the electrical outputs of said sensor for measuring signals associated with human tissue impedance, the first and second electrodes are configured to enable contact with the skin surface of the human body. At the same time, the operational stability and sensitivity of sensors are increased.

11 Claims, 3 Drawing Sheets

(51) Int. Cl.
  *A61B 5/0531* (2021.01)
  *A61B 5/00* (2006.01)
  *A61B 5/021* (2006.01)

(52) U.S. Cl.
  CPC ......... *A61B 5/02141* (2013.01); *A61B 5/6824* (2013.01); *A61B 2562/0247* (2013.01); *A61B 2562/164* (2013.01)

(56) References Cited

U.S. PATENT DOCUMENTS

| | | |
|---|---|---|
| 2004/0065158 A1 | 4/2004 | Schrepfer et al. |
| 2006/0116564 A1 | 6/2006 | Mintchev et al. |
| 2007/0287923 A1 | 12/2007 | Adkins et al. |
| 2014/0206976 A1* | 7/2014 | Thompson ......... A61B 5/04087 600/391 |
| 2017/0011210 A1* | 1/2017 | Cheong ................ A61B 5/0022 |

FOREIGN PATENT DOCUMENTS

| | | |
|---|---|---|
| CN | 104095622 A | 10/2014 |
| CN | 104523285 A | 4/2015 |
| RU | 2283025 C2 | 6/2006 |
| RU | 2365515 C1 | 8/2009 |
| RU | 2378983 C1 | 1/2010 |
| RU | 2454924 C2 | 7/2012 |
| TW | 524977 B | 3/2003 |
| WO | 03/017834 A1 | 3/2003 |
| WO | 2014187937 A1 | 11/2014 |

\* cited by examiner

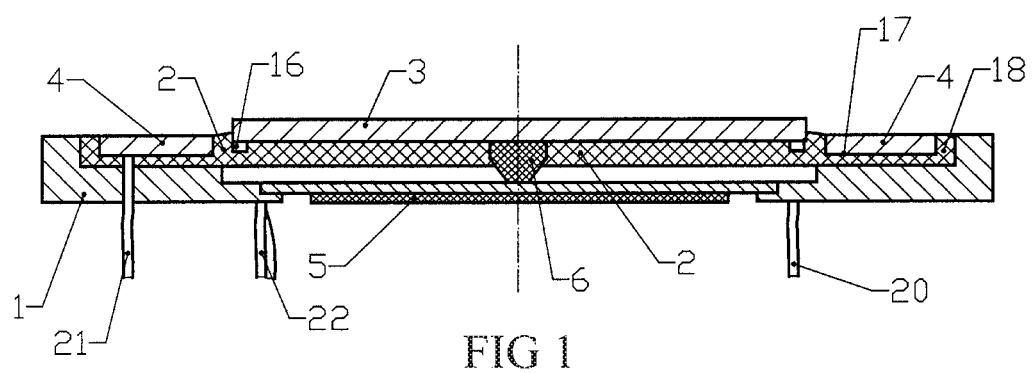
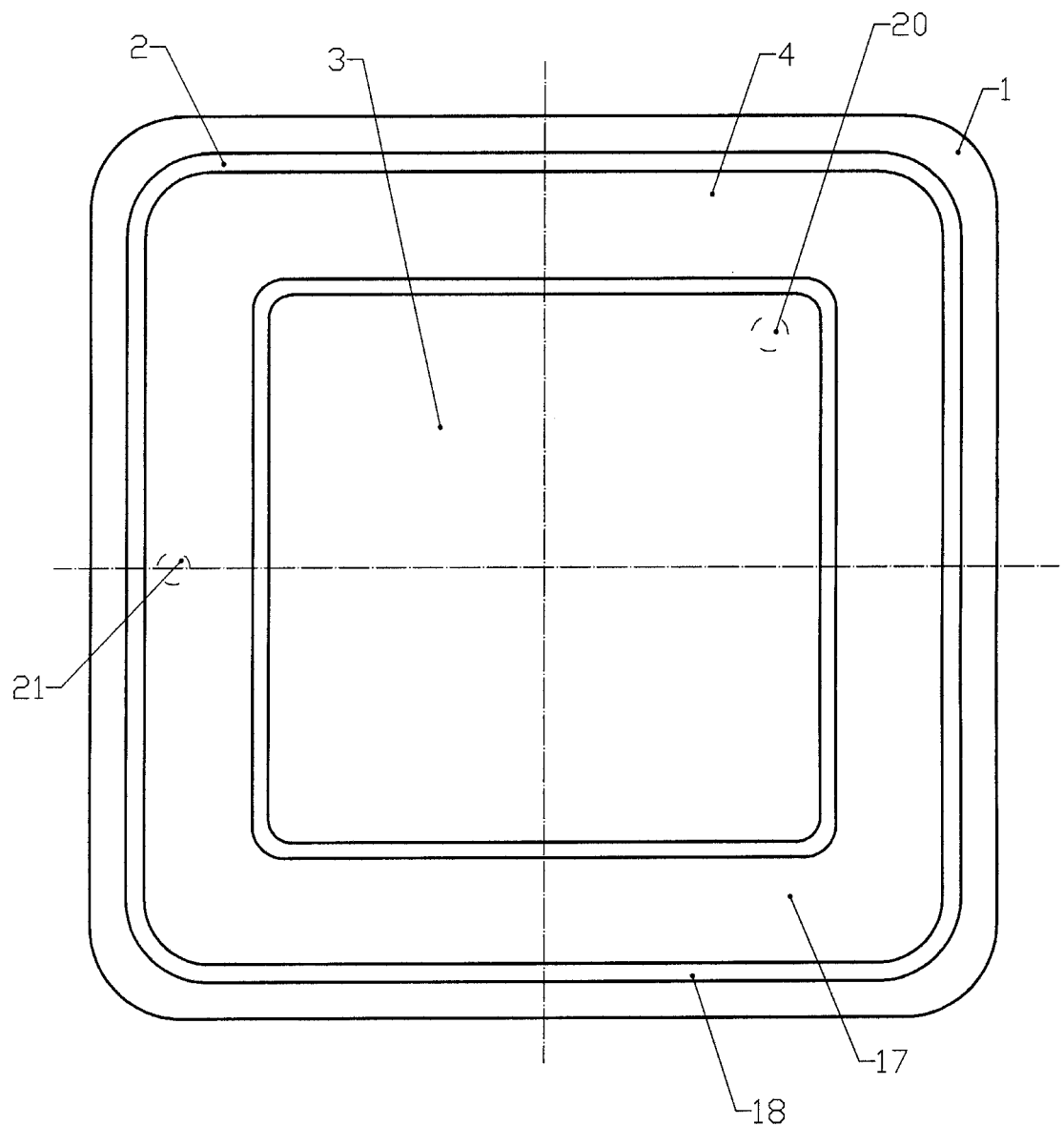

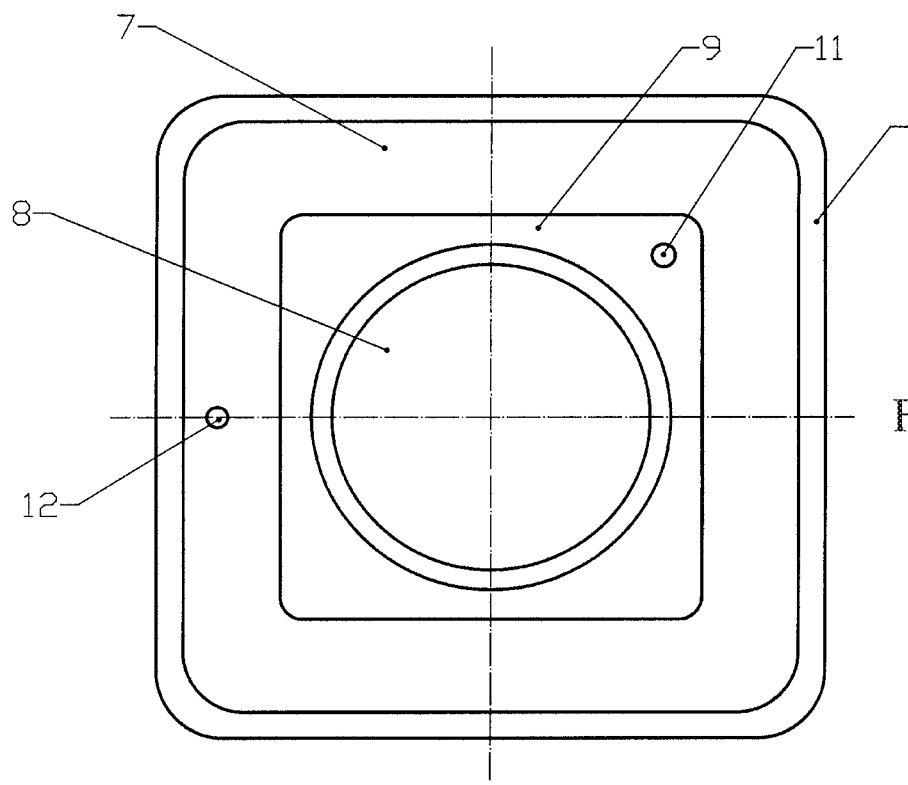
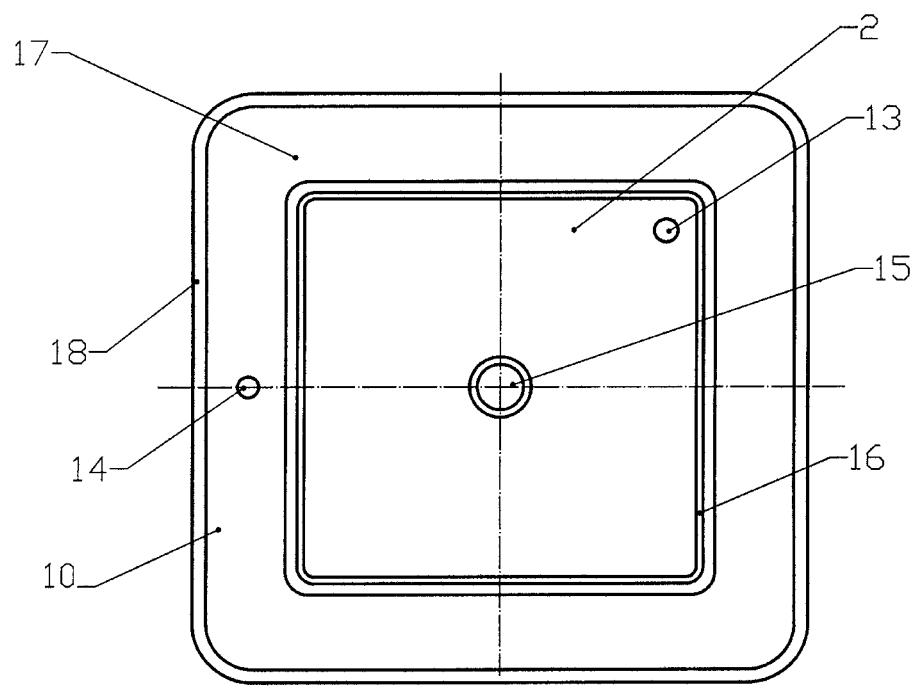

SENSOR UNIT

RELATED APPLICATIONS

This Application is a Continuation application of International Application PCT/RU2016/000269, filed on May 4, 2016, which in turn claims priority to Russian Patent Applications No. RU 2015117066, filed May 6, 2015, both of which are incorporated herein by reference in their entirety.

FIELD OF THE INVENTION

The invention relates to medicine, in particular to measurements made for diagnostic purposes, more specifically, to pressure measurements aimed at identifying human body hemodynamic parameters and measurements of human tissues impedance.

BACKGROUND OF THE INVENTION

An increasing number of devices for diagnosing human state in the process of natural behavior are developed in recent times. The diagnostics is performed by using several sensors, which monitor various human vital signs, including hemodynamic parameters and impedance of human body tissues.

Various methods and embodiments of monitoring systems are known, wherein different sensors are used as separate devices.

For example, application US2004039254 (published 26 Feb. 2004, IPC A61B05/00) describes a monitoring device comprising various sensors, which can be installed in a device attached to the forearm. The device can include a body tissue impedance sensor and a pressure sensor for measuring heart rate, which are manufactured separately.

A lot of other embodiments of pressure and impedance sensors to be implemented separately from each other are known.

For example, application US20070287923 (published 13 Dec. 2007, IPC A61B5/021) describes the embodiment of a pressure sensor mounted on human wrist and intended for plethysmography. The sensor comprises a case with a piezoelectric element mounted therein. A sensitive movable element enabling a skin contact, relays the pressure to the piezoelectric element through a central support, thus causing said piezoelectric element to bend.

Another embodiment of a sensor for measuring human skin impedance is known from application US20040065158 (published 8 Apr. 2004, IPC G01N1/00). The sensor comprises a base with a flat ring electrode mounted thereon; also mounted on the same base inside said ring electrode is a second flat strip electrode, its width being much smaller than its length.

However, no technical solutions combining a pressure sensor and an impedance sensor in a single unit are known to the applicants.

Yet, the use of separate sensors enlarges the dimensions of the device in which they are installed, and makes the application of the device more complex.

SUMMARY OF THE INVENTION

The technical result achieved by the claimed invention consists of reducing the dimensions of sensor unit by making it smaller compared to a device containing separate sensors. Coincidently, the operation of sensors combined into one unit becomes more stable, while their sensitivity increases.

A sensor unit, which makes part of a device attached to a skin surface segment of a human body and comprises a pressure sensor and a sensor for measuring a signal associated with an impedance of the associated human body segment, includes a base with a recess, wherein a piezoelectric element of pressure sensor is fixed. The unit also includes a flexible membrane mounted on the base with a part of the flexible membrane overlapping said recess. A first electrode and a second electrode are attached to the outer surface of the membrane. The first electrode is mounted opposite the recess on the part of the flexible membrane overlapping said recess and is capable of moving together with the membrane. The second electrode surrounds the first electrode and is attached to another part of the membrane not overlapping the recess, and is therefore immovable. A central support is mounted between the first electrode and the piezoelectric element. The first and second electrodes are aligned so as to permit contact with the skin surface of the human body, and are connected to the electrical outputs of said sensor for measuring the signal associated with the impedance.

This sensor unit structurally integrates a pressure sensor, for example, blood pressure sensor, and a sensor for measuring a signal associated with human tissue impedance, thus making it possible to measure the above parameters simultaneously. Such an embodiment needs a smaller skin surface area for accommodating the sensors due to mutual overlaying of pressure sensor elements and impedance sensor elements, as well as an optimal geometrical alignment of sensor elements. The second electrode surrounds the first movable electrode, thus making the whole device compact at a maximum possible area of its electrodes and the sensing element of pressure sensor, which is represented by the first electrode. Said first movable electrode serves as one of the electrodes of the sensor for measuring a signal associated with human tissue impedance and, at the same time, an element that senses pressure and transfers it to the piezoelectric element of pressure sensor.

The sensor unit embodiment affords opportunity to increase the operational stability of each of the two sensors. This result is achieved both by expanding the skin surface contact area and by placing both electrodes of the sensor for measuring a signal associated with an impedance on a flexible membrane. The placement of the first movable electrode on the flexible membrane ensures a stable skin surface contact provided by elastic properties of the membrane. The immovable sensor is mounted at the edge of the membrane made of an elastic material attached to the base. The elastic membrane material under the immovable sensor provides a more stable contact between the electrode surface and the skin surface of the human body.

The sensitivity of sensors is increased due to the fact that the human body skin surface contact area of each sensor is maximized within a given contact area of the sensor unit.

In a particular case, said recess in the base is surrounded by a groove, which accommodates the flexible membrane, with the second electrode attached thereon and above said recess. Such positioning of the membrane is technologically more effective since it decreases the transverse dimension of the sensor unit.

Besides, the membrane can be mounted on the base in a manner that makes the whole sensor unit watertight.

In one embodiment, an opening for an electric output of the first electrode can be made in the membrane.

More particularly, the first electrode can be attached to the membrane in a manner that provides a sealed connection, which increases the overall tightness of the sensor unit.

Thereat, an opening can be made in the membrane for electric output of the first electrode.

The membrane may also comprise an opening for installing said central support. In this case, the pressure from the first electrode is transferred directly to the piezoelectric element.

In one embodiment, the flexible membrane is made of a dielectric material.

The second electrode can be mounted with a gap separating it from the first electrode.

More particularly, when the sensor is in a static condition, the outer surface of the first electrode is raised above the surface of the second electrode by 0.1-3 mm.

Besides, the central support can be mounted roughly at the center of the piezoelectric element.

BRIEF DESCRIPTION OF THE DRAWINGS

The invention is illustrated by the following graphic materials:

FIG. 1 shows a sectional view of the sensor unit,
FIG. 2 gives a top view of the sensor unit,
FIG. 3 presents a base drawing (upper view),
FIG. 4 presents a membrane drawing (upper view)

DETAILED DESCRIPTION OF THE PREFERRED EMBODIMENTS

Figure 5:
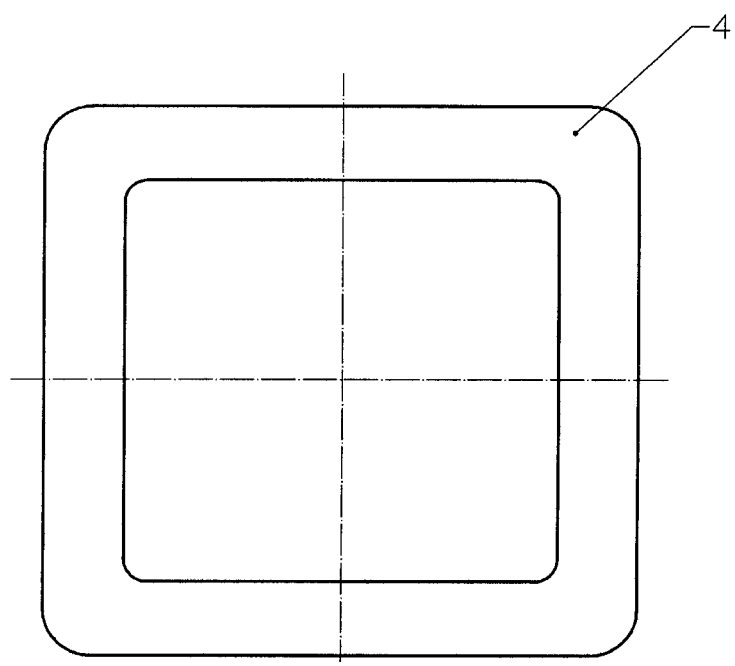
FIG. 5 presents a second electrode drawing (upper view)
Figure 6:
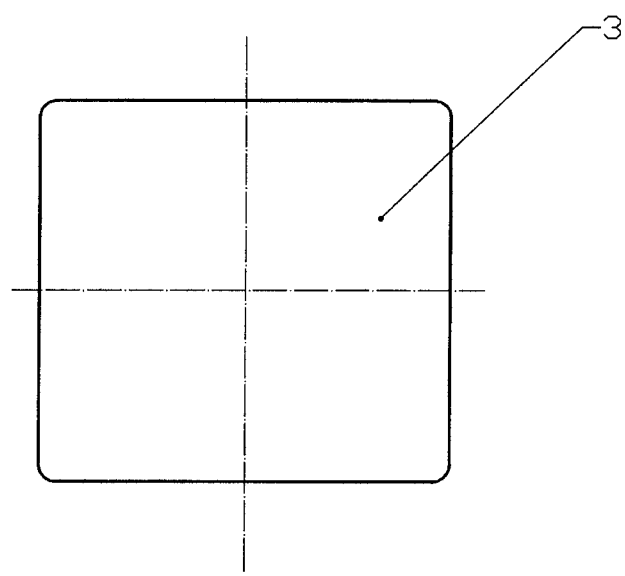
FIG. 6 shows a first electrode drawing (upper view)

The sensor unit of the device includes base 1 with recess 8 (FIG. 1, FIG. 2 and FIG. 3), wherein piezoelectric element 5 of pressure sensor is mounted on flange 9; and flexible membrane 2 (FIG. 1, FIG. 2 and FIG. 4) mounted on base 1 with a part of the flexible membrane 2 overlapping recess 8. Membrane 2 can be either mounted on the base, or glued to the base in recess 7. First electrode 3 and second electrode 4 are attached to the outer surface of membrane 2 (FIG. 1, FIG. 2, FIG. 5 and FIG. 6). Both electrodes may be glued to membrane 2. Membrane 2 has groove 16 (FIG. 1, FIG. 4) on its movable part, which enhances its flexibility. It provides a sufficient mobility at the spot, where movable electrode 3 is mounted. Movable electrode 3 is glued to membrane 2. Gluing of membrane and electrodes provides the integrity of sensor unit and makes it watertight. Membrane 2 is made of a dielectric material, for example, rubber-based. Membrane 2 also includes groove 23 for mounting immovable electrode 4. First electrode 3 is mounted opposite recess 8. Second immovable electrode 4 is glued in groove 10 of membrane 2 around first movable electrode 3, being attached to another part of membrane 2 not overlapping recess 8. Mounting of the second electrode on a rubber-based material of the membrane provides stability of contact between the second electrode and the human body skin surface. Additionally, such an embodiment makes the sensor unit watertight.

Figure 7:
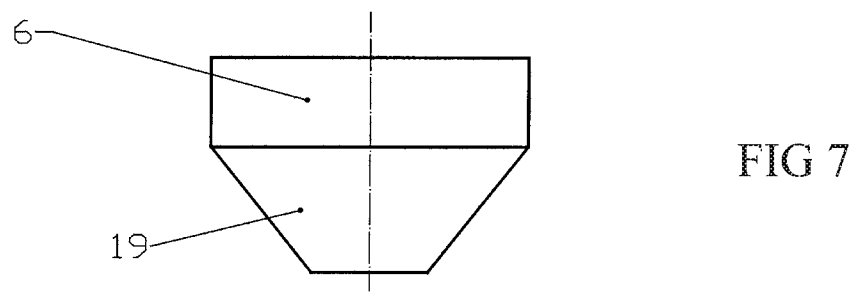
FIG. 7 presents a central support drawing (side view).

Central support 6 is mounted between first electrode 3 and piezoelectric element 5. Central support 6 has a conical section (FIG. 1 and FIG. 7). The conical section of central support 6 is placed into conical hole 15 (FIG. 4) of membrane 2, which enables a snug fit of central support 6. Central support 6 is made of a dielectric material. Electric terminals 20 and 21 of the sensor for measuring a signal associated with an impedance are connected, respectively, to first electrode 3 and second electrode 4. Pressure sensor terminals 22 are connected to piezoelectric element 5 (FIG. 1). Terminal 20 of first electrode 3 passes through opening 13 in membrane 2 (FIG. 4) and opening 11 in base 1 (FIG. 3). Accordingly, terminal 21 of immovable electrode 4 passes through opening 14 in membrane 2 and opening 12 in base 1 (FIG. 3 and FIG. 4). When the sensor is in a static condition, the outer surface of first movable electrode 3 is raised above the surface of second immovable electrode 4 by 0.1 to 3 mm, which provides a tight contact of electrodes 3 and 4 with skin, and stabilizes the functioning of pressure sensor.

The sensor unit can be employed in devices that require data on the impedance of skin and subcutaneous layers of a human body segment, as well as pressure needed, for example, to identify the hemodynamic parameters of the human body. The sensor unit may be disposed on skin surfaces of various parts of human body, including, but not limited to cervical spine, chest and extremities. The sensor unit is especially suitable for use in wearable devices attached to human body segments having a limited flat skin surface area, for example, to the wrist.

The sensor unit can be attached to the skin surface of a human body by means of various fastening devices, for example, straps. First electrode 3 and second electrode 4 of the sensor unit must be attached in a manner providing their reliable contact with the skin surface of the human body. The contact of first electrode 3 and second electrode 4 of the sensor for measuring a signal associated with an impedance with the skin surface of the human body enables measurements of biological tissue impedance using known methods. The contact of first movable electrode 3 with the skin surface of the human body provides for transfer of skin pulsations caused, for example, by arterial pressure changes, from the movable electrode to the membrane, central support and piezoelectric element 5, making pressure sensor operation possible.

INDUSTRIAL APPLICABILITY

The pressure sensor unit has a simple scheme and is technologically efficient. The sensor unit can be employed in various monitoring devices used in medicine and health monitoring due to its small dimensions, water tightness, as well as high sensitivity of its pressure and impedance sensors.

What is claimed is:

1. A sensor unit for use in diagnostic measurements configured to be disposed on a skin surface segment of a human body, the sensor unit comprising:
    a pressure sensor comprising a piezoelectric element;
    a sensor for measuring a signal associated with an impedance of an associated human body segment;
    a base with a recess accommodating the piezoelectric element of the pressure sensor;
    a flexible membrane mounted on the base with a part of the flexible membrane overlapping the recess;
    a first electrode and a second electrode attached to an outer surface of the flexible membrane, the first electrode being positioned opposite the recess and attached on the part of the flexible membrane overlapping the recess and being capable of moving together with the part of the membrane overlapping the recess, the second electrode surrounding the first electrode and attached on another part of the membrane not overlapping the recess, the second electrode being immovable; and a central support disposed between the first electrode and the piezoelectric element;

wherein the first electrode and the second electrode are disposed to enable contact with the skin surface segment of the human body and are coupled to electrical terminals of the sensor for measuring the signal associated with the impedance.

2. The sensor unit of claim 1, wherein the second electrode is disposed on the flexible membrane above the recess.

3. The sensor unit of claim 1, wherein the flexible membrane is hermetically mounted on the base.

4. The sensor unit of claim 3, wherein the membrane comprises an opening for an electrical output of the first electrode.

5. The sensor unit of claim 1, wherein the first electrode is hermetically attached to the flexible membrane.

6. The sensor unit of claim 5, wherein the flexible membrane comprises an opening for an electrical output of the first electrode.

7. The sensor unit of claim 5, wherein the flexible membrane comprises an opening for the central support.

8. The sensor unit of claim 1, wherein the flexible membrane is made of a dielectric material.

9. The sensor unit of claim 1, wherein the second electrode and the first electrode are separated by a gap.

10. The sensor unit of claim 1, wherein an outer surface of the first electrode is raised above a surface of the second electrode by a range from 0.1 mm to 3 mm.

11. The sensor unit of claim 1, wherein the central support is disposed at a center of the piezoelectric element.

* * * * *